(12) United States Patent
Cocquerel-Deproy et al.

(10) Patent No.: US 10,875,896 B2
(45) Date of Patent: Dec. 29, 2020

(54) HEPATITIS E VIRUS ORF2 CAPSID POLYPEPTIDES AND USES THEREOF

(71) Applicants: INSERM (Institut National de la Santéet de la Recherche Médicale), Paris (FR); Institut Pasteur de Lille, Lille (FR); Centre National de la Recherche Scientifique (CNRS), Paris (FR); Universitéde Lille, Lille (FR); Centre Hospitalier Regional Universitaire de Lille, Lille (FR)

(72) Inventors: Laurence Cocquerel-Deproy, Lille (FR); Claire Montpellier, Lille (FR); Jean Dubuisson, Lille (FR); Anne Goffard, Lille (FR)

(73) Assignees: INSERM (Institut National de la Santé et de la Recherche Médicale), Paris (FR); Institut Pasteur de Lille, Lille (FR); Centre National de la Recherche Scientifique (CNRS), Paris (FR); Universitë de Lille, Lille (FR); Centre Hospitalier Regional Universitaire de Lille, Lille (FR)

( * ) Notice: Subject to any disclaimer, the term of this patent is extended or adjusted under 35 U.S.C. 154(b) by 0 days.

(21) Appl. No.: 16/482,000

(22) PCT Filed: Jan. 29, 2018

(86) PCT No.: PCT/EP2018/052149
§ 371 (c)(1),
(2) Date: Jul. 30, 2019

(87) PCT Pub. No.: WO2018/138344
PCT Pub. Date: Aug. 2, 2018

(65) Prior Publication Data
US 2019/0352342 A1    Nov. 21, 2019

(30) Foreign Application Priority Data

Jan. 30, 2017  (EP) .................................. 17305097
Jul. 28, 2017  (EP) .................................. 17306010

(51) Int. Cl.
*C07K 14/005* (2006.01)
*C07K 16/10* (2006.01)
(Continued)

(52) U.S. Cl.
CPC ............ *C07K 14/005* (2013.01); *C07K 16/10* (2013.01); *C12N 7/00* (2013.01); *G01N 33/5767* (2013.01);
(Continued)

(58) Field of Classification Search
None
See application file for complete search history.

(56) References Cited

U.S. PATENT DOCUMENTS 6,514,690 B1 *  2/2003  Li ........................ C07K 14/005
                                                              435/5

FOREIGN PATENT DOCUMENTS

WO     02/053712 A2    7/2002
WO   2012/096999 A1    7/2012

OTHER PUBLICATIONS

GenBank: AQY45720.1 (2016) capsid protein [Swine hepatitis E virus]. (Year: 2016).*
(Continued)

*Primary Examiner* — Michelle S Horning
(74) *Attorney, Agent, or Firm* — W&C IP

(57) ABSTRACT

Hepatitis E virus (HEV) is responsible for over 50% of acute viral hepatitis cases worldwide. The inventors have now identified the precise sequence of infectious particle-associated ORF2 capsid protein. Strikingly, their analyses
(Continued)

Figure 2A:
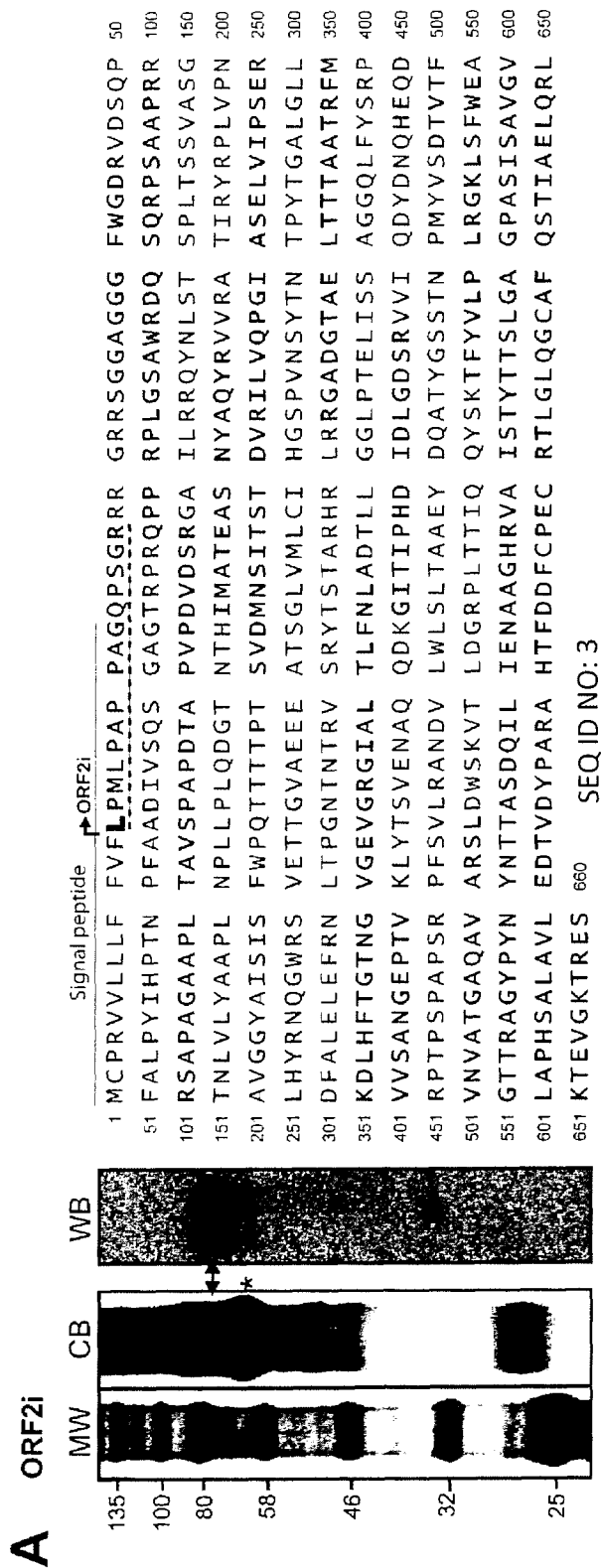

revealed that in infected patients, HEV produces three forms of the ORF2 capsid protein: ORF2i, ORF2g and ORF2c. The ORF2i protein is associated with infectious particles whereas ORF2g and ORF2c proteins are massively produced glycoproteins that are not associated with infectious particles and are the major antigens present in HEV-infected patient sera. Accordingly, the ORF2i and ORF2g proteins are thus the subject matter of the present invention as well as antibodies specific for the proteins and diagnostic assays (e.g. ELISA) for the diagnosis of Hepatitis E virus infection.

5 Claims, 8 Drawing Sheets

Specification includes a Sequence Listing.

(51) Int. Cl.
*A61K 39/29* (2006.01)
*C12N 7/00* (2006.01)
*G01N 33/576* (2006.01)

(52) U.S. Cl.
CPC .............. *C12N 2770/28122* (2013.01); *G01N 2333/02* (2013.01); *G01N 2800/26* (2013.01)

(56) References Cited

OTHER PUBLICATIONS

Zafrullah et al. Mutational Analysis of Glycosylation, Membrane Translocation, and Cell Surface Expression of the Hepatitis E Virus ORF2 Protein. Journal of Virology, May 1999, p. 4074-4082. (Year: 1999).*

Graff et al. Mutations within Potential Glycosylation Sites in the Capsid Protein of Hepatitis E Virus Prevent the Formation of Infectious Virus Particles. Journal of Virology, Feb. 2008, p. 1185-1194 (Year: 2008).*

Schofield et al.; "Identification by phage display and characterization of two neutralizing champanzee monoclonal antibodies to the hepatitis E virus capsid protein"; Journal of Virology, vol. 74, No. 12, Jun. 1, 2000, pp. 5548-5555.

Shukla et al.; "Adaptation of a Genotype 3 Hepatitis E Virus to Efficient Growth in Cell Culture Depends on an Inserted Human Gene Segment Acquired by Recombination"; Journal of Virology, vol. 86, No. 10, Mar. 7, 2012, pp. 5697-5707.

* cited by examiner

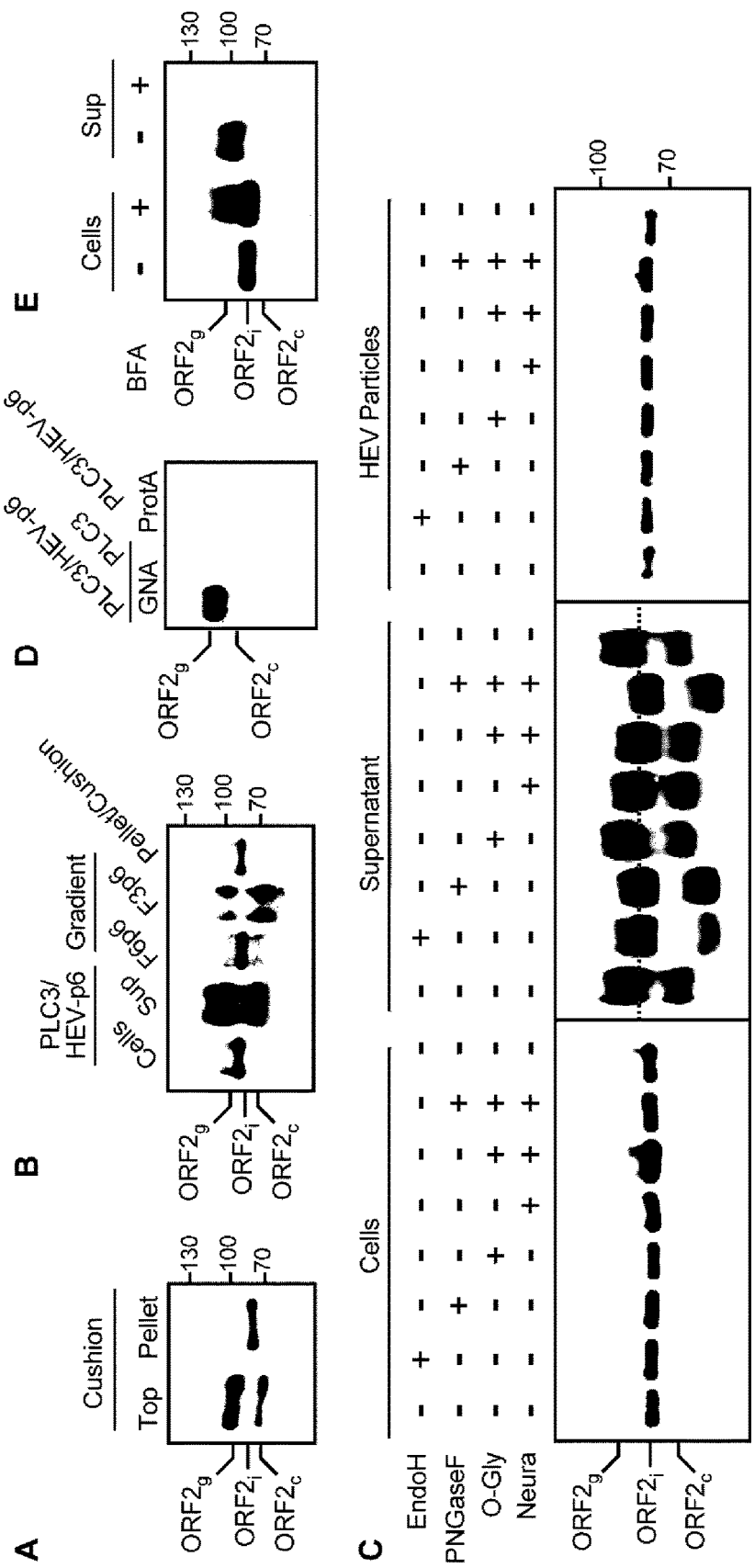
Figures 1A-E

```
                              ↓ORF2i                                              ↓ORF2g
  1  MCPRVVLLLF  FVF LPMLPAP  PAGQPSGRRR  GRR SGGAGGG  FWGDRVDSQP   50
 51  FALPYIHPTN  PFAADIVSQS   GAGTRPRQPP   RPLGSAWRDQ  SQRPSAAPRR  100
101  RSAPAGAAPL  TAVSPAPDTA   PVPDVDSRGA   ILRRQY NLS  SPLTSSVASG  150
151  TNLVLYAAPL  NPLLPLQDGT   NTHIMATEAS   NYAQYRVVRA  TIRYRPLVPN  200
201  AVGGYAISIS  FWPQTTTTPT   SVDMNSITST   DVRILVQPGI  ASELVIPSER  250
251  LHYRNQGWRS  VETTGVAEEE   ATSGLVMLCI   HGSPVNSYTN  TPYTGALGLL  300
301  DFALELEFR N LT PGNTNTRV   SRYTSTARHR   LRRGADGTAE  LTTTAATRFM  350
351  KDLHFTGTNG  VGEVGRGIAL   TLFNLADTLL   GGLPTELISS  AGGQLFYSRP  400
401  VVSANGEPTV  KLYTSVENAQ   QDKGITIPHD   IDLGDSRVVI  QDYDNQHEQD  450
451  RPTPSPAPSR  PFSVLRANDV   LWLSLTAAEY   DQATYGSSTN  PMYVSDTVTF  500
501  VNVATGAQAV  ARSLDWSKVT   LDGRPLTTIQ   QYSKTFYVLP  LRGKLSFWEA  550
551  GTTRAGYPYN  Y NTT ASDQIL  IENAAGHRVA   ISTYTTSLGA  GPASISAVGV  600
601  LAPHSALAVL  EDTVDYPARA   HTFDDFCPEC   RTLGLQGCAF  QSTIAELQRL  650
651  KTEVGKTRES  660   SEQ ID NO: 3
```

Figure 1F

HEPATITIS E VIRUS ORF2 CAPSID POLYPEPTIDES AND USES THEREOF

FIELD OF THE PRESENT INVENTION

The present invention relates to hepatitis E virus ORF2 capsid polypeptides and uses thereof.

BACKGROUND OF THE PRESENT INVENTION

Hepatitis E virus (HEV) is the leading cause of enterically transmitted viral hepatitis globally, and is responsible for 20 million infections and 70,000 deaths every year[1]. Though HEV infection is usually self-resolving, severe forms or chronic infections have been described, mainly in immuno-compromised patients. A high rate of mortality has also been reported among pregnant women. HEV infection has also been associated with extrahepatic disorders, including renal and neurological disorders[2]. Four genotypes (gt) are pathogenic in humans. Gt1 and gt2 exclusively infect humans, while gt3 and gt4 are zoonotic and mainly infect animals that may transmit the virus to humans. Recently, gt3 infections have been emerging in the Western world, likely due to contaminated blood transfusions and the consumption of contaminated food[1]. The diagnosis of hepatitis E is based on the detection of anti-HEV antibodies and/or viral RNA in patient serum[3]. Recently, a new assay based on detecting the HEV capsid protein antigen was developed (Wantaï Biologicals), especially for laboratories with no molecular diagnosis facilities.

HEV is a quasi-enveloped, positive-sense RNA virus expressing three open reading frames (ORFs): ORF1, ORF2 and ORF3[1]. ORF1 encodes the ORF1 non-structural polyprotein, which contains several functional domains essential for viral replication. ORF2 encodes the ORF2 viral capsid protein, which is involved in particle assembly, binding to host cells and eliciting neutralizing antibodies. ORF3 encodes a small multifunctional phosphoprotein involved in virion morphogenesis and egress. Although HEV is a non-enveloped virus in bile and feces, patient serum and cell culture-produced particles have been described to be associated with cellular lipids, as for Hepatitis A virus[4], and display the ORF3 protein at their surface[5].

The growth of HEV in cell culture has been proven to be very difficult[5]. However, several HEV strains have been adapted to cell culture, including the gt3 Kernow C-1 strain, which contains an insertion of a 58-aa human S17 ribosomal protein[6]. Although these systems have led to increased understanding of the HEV lifecycle, they still produce low infectious titers, limiting direct biochemical analysis of viral proteins and infectious material. Notably, the exact sequence of infectious particle-associated ORF2 protein is unknown. In addition, the ultrastructure of particles has never been robustly studied by immune electron microscopy.

SUMMARY OF THE PRESENT INVENTION

The present invention relates to hepatitis E virus ORF2 capsid polypeptides and uses thereof. In particular, the present invention is defined by the claims.

DETAILED DESCRIPTION OF THE PRESENT INVENTION

Hepatitis E virus (HEV) infection is a major cause of acute hepatitis worldwide. Approximately 2 billion people live in areas endemic for HEV and are at risk of infection. The HEV genome encodes 3 proteins, including the ORF2 capsid protein. Detailed analyses of the HEV lifecycle has been hampered by the lack of an efficient viral culture system.

The inventors performed studies with gt3 HEV cell culture-produced particles (HEVcc) and patient blood and stool samples. Samples were fractionated on iodixanol gradients and cushions. Infectivity assays were performed in vitro and in human liver chimeric mice. Proteins were analyzed by biochemical and proteomic approaches. Infectious particles were analyzed by transmission electron microscopy. HEV antigen levels were measured with the Wantaï ELISA.

The inventors developed an efficient cell culture system and isolated HEV particles that were infectious in vitro and in vivo. Using transmission electron microscopy, they defined the ultrastructure of HEVcc and particles from patient sera and stool samples. They also identified the precise sequence of the infectious particle-associated ORF2 capsid protein (ORF2i) and the sequence of the ORF2g protein. Indeed, in cultured cells and in samples from patients, HEV produced 3 forms of the ORF2 capsid protein: infectious/intracellular ORF2 (ORF2i), glycosylated ORF2 (ORF2g), and cleaved ORF2 (ORF2c). The ORF2i protein associated with infectious particles, whereas the ORF2g and ORF2c proteins were massively secreted glycoproteins not associated with infectious particles. ORF2g and ORF2c were the most abundant antigens detected in sera from patients.

Thus the inventors developed a cell culture system and characterized HEV particles; they identified 3 ORF2 capsid proteins (ORF2i, ORF2g, and ORFc). These findings will advance our understanding of the HEV lifecycle and improve diagnosis.

Accordingly, the first object of the present invention relates to a hepatitis E virus ORF2 capsid polypeptide (ORF2i) consisting of an amino acid sequence having at least 90% of identity with the amino acid sequence as set forth in SEQ ID NO:1.

SEQ ID NO: 1:
LPMLPAPPAGQPSGRRRGRRSGGAGGGFWGDRVDSQPFFALPYIHPTNPFA
ADIVSQSGAGTRPRQPPRPLGSAWRDQSQRPSAAPRRRSAPAGAAPLTAV
SPAPDTAPVPDVDSRGAILRRQYNLSTSPLTSSVASGTNLVLYAAPLNPL
LPLQDGTNTHIMATEASNYAQYRVVRATIRYRPLVPNAVGGYAISISFWP
QTTTTPTSVDMNSITSTDVRILVQPGIASELVIPSERLHYRNQGWRSVET
TGVAEEEATSGLVMLCIHGSPVNSYTNTPYTGALGLLDFALELEFRNLTP
GNTNTRVSRYTSTARHRLRRGADGTAELTTTAATRFMKDLHFTGTNGVGE
VGRGIALTLFNLADTLLGGLPTELISSAGGQLFYSRPVVSANGEPTVKLY
TSVENAQQDKGITIPHDIDLGDSRVVIQDYDNQHEQDRPTPSPAPSRPFS
VLRANDVLWLSLTAAEYDQATYGSSTNPMYVSDTVTFVNVATGAQAVARS
LDWSKVTLDGRPLTTIQQYSKTFYVLPLRGKLSFWEAGTTRAGYPYNYNT
TASDQILIENAAGHRVAISTYTTSLGAGPASISAVGVLAPHSALAVLEDT
VDYPARAHTFDDFCPECRTLGLQGCAFQSTIAELQRLKTEVGKTRES

In some embodiments, the ORF2i polypeptide of the present invention is not glycosylated. As used herein, the term "glycosylated" with respect to a polypeptide means that a carbohydrate moiety is present at one or more sites of the polypeptide molecule. In particular, a glycosylated polypeptide refers to a polypeptide that is typically modified by N-glycan or O-glycan addition.

According to the invention a first amino acid sequence having at least 90% of identity with a second amino acid sequence means that the first sequence has 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

According to the invention, the mass of the ORF2i polypeptide of the present invention is approximately 80 kDa.

The second object of the present invention relates to a hepatitis E virus ORF2 capsid polypeptide (ORF2g) consisting of an amino acid sequence having at least 90% of identity with the amino acid sequence as set forth in SEQ ID NO:2.

SEQ ID NO: 2:
SGGAGGGFWGDRVDSQPFALPYIHPTNPFAADIVSQSGAGTRPRQPPRPL

GSAWRDQSQRPSAAPRRRSAPAGAAPLTAVSPAPDTAPVPDVDSRGAILR

RQYNLSTSPLTSSVASGTNLVLYAAPLNPLLPLQDGTNTHIMATEASNYA

QYRVVRATIRYRPLVPNAVGGYAISISFWPQTTTTPTSVDMNSITSTDVR

ILVQPGIASELVIPSERLHYRNQGWRSVETTGVAEEEATSGLVMLCIHGS

-continued
PVNSYTNTPYTGALGLLDFALELEFRNLTPGNTNTRVSRYTSTARHRLRR

GADGTAELTTTAATRFMKDLHFTGTNGVGEVGRGIALTLFNLADTLLGGL

PTELISSAGGQLFYSRPVVSANGEPTVKLYTSVENAQQDKGITIPHDIDL

GDSRVVIQDYDNQHEQDRPTPSPAPSRPFSVLRANDVLWLSLTAAEYDQA

TYGSSTNPMYVSDTVTFVNVATGAQAVARSLDWSKVTLDGRPLTTIQQYS

KTFYVLPLRGKLSFWEAGTTRAGYPYNYNTTASDQILIENAAGHRVAIST

YTTSLGAGPASISAVGVLAPHSALAVLEDTVDYPARAHTFDDFCPECRTL

GLQGCAFQSTIAELQRLKTEVGKTRES

In some embodiments, the ORF2g polypeptide of the present invention is glycosylated. As used herein, the term "glycosylated" with respect to a polypeptide means that a carbohydrate moiety is present at one or more sites of the polypeptide molecule. In particular, a glycosylated polypeptide refers to a polypeptide that is typically modified by N-glycan or O-glycan addition.

According to the invention, the mass of the ORF2g polypeptide of the present invention is approximately 90-100 kDa.

In some embodiments, the ORF2i or ORF2g polypeptide of the present invention can be produced by conventional automated peptide synthesis methods or by recombinant expression. General principles for designing and making proteins are well known to those of skill in the art.

Another object of the present invention relates to an isolated, synthetic or recombinant nucleic acid encoding for the ORF2i or ORF2g polypeptide of the present invention. In some embodiments, the nucleic acid of the present invention is a DNA or RNA molecule, which may be included in any suitable vector, such as a plasmid, cosmid, episome, artificial chromosome, phage or a viral vector. The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

Another object of the present invention relates to a host cell which has been transfected, infected or transformed by a nucleic acid molecule and/or a vector according to the invention. The term "transfection" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transfected". The nucleic acid molecule of the present invention may be used to produce a polypeptide of the present invention in a suitable expression system. The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculovirus vectors, and mammalian host cells and vectors.

The present invention also relates to an antibody specific for the ORF2i or ORF2g polypeptide of the present invention.

As used herein, the term "antibody" has its general meaning in the art and refers to any antibody-like molecule that has an antigen binding region, and this term includes antibody fragments that comprise an antigen binding domain such as Fab', Fab, F(ab')2, and single domain antibodies (DABs), In natural antibodies, two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules. The term "affinity", as used herein, means the strength of the binding of an antibody to an epitope. The affinity of an antibody is given by the dissociation constant Kd, defined as $[Ab]\times[Ag]/[Ab\text{-}Ag]$, where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

In some embodiments, the antibody is a polyclonal antibody or a monoclonal antibody. Monoclonal antibodies may be generated using the method of Kohler and Milstein (Nature, 256:495, 1975). To prepare monoclonal antibodies useful in the invention, a mouse or other appropriate host animal (e.g. mouse, goat, camelid . . . ) is immunized at suitable intervals (e.g., twice-weekly, weekly, twice-monthly or monthly) with a relevant viral antigenic form. For instance, the viral antigenic form is typically prepared according to the following method: an amount of viral particles can be prepared according by the culture system of EXAMPLE and then purified on iodixanol cushion and finally treated with an amount of trypsin and sodium deoxycholate (DOCA). Alternatively, the antigenic form directly consists in a peptide that derives from the polypeptide of the present invention. The animal may be administered a final "boost" of the antigenic form within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, immunofluorescence, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

In a further aspect, detection of the ORF2i or ORF2g polypeptide of the present invention in a sample may be particularly of interest for diagnostic purposes. In particular, detection of the ORF2i or ORF2g polypeptide of the present invention is suitable for determining presence of infectious particles of hepatitis E virus in a sample. More particularly, detection of the ORF2i or ORF2g polypeptide of the present invention is suitable for diagnosing hepatitis E virus infection in a subject.

As used herein, the term "sample" includes any solid or fluid sample, liable to contain infectious particles of hepatitis E virus. In some embodiments, the sample is selected from the group consisting of ascites; urine; saliva; sweat; milk; synovial fluid; peritoneal fluid; amniotic fluid; percerebrospinal fluid; lymph fluid; lung embolism; cerebrospinal fluid; and pericardial fluid. In some embodiments, the sample is a faeces samples. In some embodiments, the sample is a urine sample. In some embodiments, the sample is a blood sample. As used herein the term "blood sample" means any blood sample derived from the subject. Collections of blood samples can be performed by methods well known to those skilled in the art. For example, the subject's blood can be drawn by trained medical personnel directly into anti-coagulants such as citrate and EDTA. The whole blood can be separated into the plasma portion, the cells, and platelets portion by refrigerated centrifugation at 3500×G for 2 minutes. After centrifugation, the supernatant is the plasma.

The antibodies of the present invention are particularly suitable for detecting the presence of the ORF2i or ORF2g polypeptide of the present invention in a sample.

Accordingly a further object of the present invention relates to a method for detecting the presence of the ORF2i or ORF2g polypeptide of the present invention in a sample comprising contacting the sample with the antibody of the present invention under conditions that allow an immunocomplex of the polypeptide and the antibody to form wherein detection of the immunocomplex indicates the presence of the polypeptide in the sample.

More particularly, a further object of the present invention relates to a method for detecting the presence of infectious particles of hepatitis E virus in a sample comprising contacting the sample with the antibody having specificity for the ORF2i polypeptide under conditions that allow an immunocomplex of the antibody and the infectious particles to form wherein detection of the immunocomplex indicates the presence of the infectious particles in the sample.

In some embodiments, the detecting methods of the present invention may further comprises contacting the sample with antibodies having specificity for the ORF2c polypeptide (i.e. the mass of the ORF2c polypeptide is approximately 75 kDa).

The detecting methods of the present invention are particularly suitable for diagnosing acute HEV infection, recent HEV infection, chronic HEV infection or a weak active HEV infection. The detecting methods of the present invention are also suitable for diagnosing cleared HEV infection, which is characterized by the detection of the ORF2g polypeptide (along with the detection of the ORF2c polypeptide) but without detection of the ORF2i polypeptide.

Assays and conditions for the detection of immunocomplexes are known to those of skill in the art. Such assays include, for example, competition assays, direct reaction assays sandwich-type assays and immunoassays (e.g. ELISA). The assays may be quantitative or qualitative. There are a number of different conventional assays for detecting formation of an antibody-peptide complex comprising a polypeptide of the present invention. For example, the detecting step can comprise performing an ELISA assay, performing a lateral flow immunoassay, performing an agglutination assay, analyzing the sample in an analytical rotor, or analyzing the sample with an electrochemical, optical, or opto-electronic sensor. These different assays are well-known to those skilled in the art.

For example, any of a number of variations of the sandwich assay technique may be used to perform an immunoassay. Briefly, in a typical sandwich assay, a first antibody of the present invention is immobilized on a solid surface and the sample to be tested is brought into contact with the immobilized antibody for a time and under conditions allowing formation of the immunocomplex. Following incubation, a second antibody of the present invention that is labeled with a detectable moiety is added and incubated under conditions allowing the formation of a ternary complex between any immunocomplex and the labeled antibody. Any unbound material is washed away, and the presence of polypepyide in the sample is determined by observation/detection of the signal directly or indirectly produced by the detectable moiety. Detection may be either qualitative or quantitative. Methods for labeling biological molecules such as antibodies are well-known in the art (see, for example, "Affinity Techniques. Enzyme Purification: Part B", Methods in EnzymoL, 1974, Vol. 34, W. B. Jakoby and M. Wilneck (Eds.), Academic Press: New York, N.Y.; and M. Wilchek and E. A. Bayer, Anal. Biochem., 1988, 171: 1-32). The most commonly used detectable moieties in immunoassays are enzymes and fluorophores. In the case of an enzyme immunoassay (EIA or ELISA), an enzyme such as horseradish perodixase, glucose oxidase, beta-galactosidase, alkaline phosphatase, and the like, is conjugated to the second antibody, generally by means of glutaraldehyde or periodate. The substrates to be used with the specific enzymes are generally chosen for the production of a detectable color change, upon hydrolysis of the corresponding enzyme. In the case of immunofluorescence, the second antibody is chemically coupled to a fluorescent moiety without alteration of its binding capacity. After binding of the fiuorescently labeled antibody to the immunocomplex and removal of any unbound material, the fluorescent signal generated by the fluorescent moiety is detected, and optionally quantified. Alternatively, the second antibody may be labeled with a radioisotope, a chemiluminescent moiety, or a bioluminescent moiety. In some embodiments, the assay utilizes a solid phase or substrate to which the antibody of the present invention is directly or indirectly attached. Accordingly in some embodiments, the antibody of the present invention is attached to or immobilized on a substrate, such as a solid or semi-solid support. The attachment can be covalent or non-covalent, and can be facilitated by a moiety associated with the polypeptide that enables covalent or non-covalent binding, such as a moiety that has a high affinity to a component attached to the carrier, support or surface. In some embodiments, the substrate is a bead, such as a colloidal particle (e.g., a colloidal nanoparticle made from gold, silver, platinum, copper, metal composites, other soft metals, core-shell structure particles, or hollow gold nanospheres) or other type of particle (e.g., a magnetic bead or a particle or nanoparticle comprising silica, latex, polystyrene, polycarbonate, polyacrylate, or PVDF). Such particles can comprise a label (e.g., a colorimetric, chemiluminescent, or fluorescent label) and can be useful for visualizing the location of the polypeptides during immunoassays. In some embodiments, the substrate is a dot blot or a flow path in a lateral flow immunoassay device. For example, the antibody of the present invention can be attached or immobilized on a porous membrane, such as a PVDF membrane (e.g., an Immobilon™ membrane), a nitrocellulose membrane, polyethylene membrane, nylon membrane, or a similar type of membrane. In some embodiments, the substrate is a flow path in an analytical rotor. In some embodiments, the substrate is a tube or a well, such as a well in a plate (e.g., a microtiter plate) suitable for use in an ELISA assay. Such substrates can comprise glass, cellulose-based materials, thermoplastic polymers, such as polyethylene, polypropylene, or polyester, sintered structures composed of particulate materials (e.g., glass or various thermoplastic polymers), or cast membrane film composed of nitrocellulose, nylon, polysulfone, or the like. A substrate can be sintered, fine particles of polyethylene, commonly known as porous polyethylene, for example, 0.2-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

A further object of the present invention relates to a kit or device comprising at least one antibody of the present invention (immobilized or not on a solid support as described above). In some embodiments, the kit comprises an antibody having specificity for the ORF2i polypeptide. In some embodiments, the kit comprises an antibody having specificity for the ORF2g polypeptide. In some embodiments, the kit comprises an antibody having specificity for the ORF2i polypeptide and antibody having specificity for the ORF2g polypeptide. In some embodiments, the kit of the present invention further comprises an antibody having specificity for the ORF2c polypeptide. Examples of kits include but are not limited to ELISA assay kits, and kits comprising test strips and dipsticks. In some embodiments, the kits described herein further comprise reference values of the levels of the polypeptide or infectious particles. The reference values are typically average levels in samples from a population of healthy individuals. In some embodiments, the kits described herein further comprise at least one sample collection container for sample collection. Collection devices and container include but are not limited to syringes, lancets, BD VACUTAINER® blood collection tubes. In some embodiments, the kits described herein further comprise instructions for using the kit and interpretation of results.

The invention will be further illustrated by the following figures and examples. However, these examples and figures should not be interpreted in any way as limiting the scope of the present invention.

FIGURES

FIG. 1: Characterization of the different ORF2 products. (A) Detection by WB of ORF2 proteins in the top and pellet of the PLC3/HEV-p6 cell supernatant purified onto iodixanol cushion. (B) Comparison of ORF2 products expressed in the cell lysates and supernatant of PLC3/HEV-p6 cells, in infectious fraction 6 (F6p6) and non-infectious fraction 3 (F3p6) from iodixanol gradient, and in the pellet of PLC3/HEV-p6 cell supernatant purified on the iodixanol cushion. (C) PLC3/HEV-p6 cell lysate, supernatant and purified HEV particles were denatured and digested with indicated glycosidases (+) or not (−). The dashed line shows the migration shift of ORF2 proteins following glycosidase treatment. (D) ORF2 protein detection after incubation of the supernatant of PLC3/HEV-p6 or PLC3 cells with GNA- or ProteinA-conjugated agarose beads. (E) PLC3/HEV-p6 cells were treated (+) or not (−) with Brefeldin A (BFA, 16 h, 1 µg/ml) and the ORF2 protein expression in cells and supernatant was analyzed. (F) Sequence of ORF2 proteins analyzed by nanoLC-MS/MS. The dashed line corresponds to the signal peptide. Frames indicate potential N-glycosylation sites. The first aa of ORF2i and ORF2g identified by TMPP-Ac-OSu labeling are in bold.

FIG. 2: Characterization of the different ORF2 products. Viral particles purified on iodixanol cushion and ORF2g/ORF2c proteins immunoprecipitated with an anti-ORF2 antibody (4B2) were resolved by SDS-PAGE. Colloidal blue (CB) staining and WB are shown. The arrow indicates ORF2i (A), ORF2g (B) and ORF2c (C). The asterisk indicates human albumin. H and L indicate the heavy and light chains of immunoglobulins used in IP. ORF2 forms were digested in-gel with trypsin or AspN and analyzed by nanoLC-MS/MS. Peptide covering is highlighted in grey on the sequence of each ORF2 product. Dashed lines correspond to semi-trypsic and semi-AspN peptides. Lett[14] and Ser[34] in bold correspond to the first aa of ORF2i (A) and ORF2g (B), respectively, that were identified by semi-specific cleavage and TMPP-Ac-OSu labeling. No evidence was found for the N-terminal part of ORF2c (C).

Figure 3A:
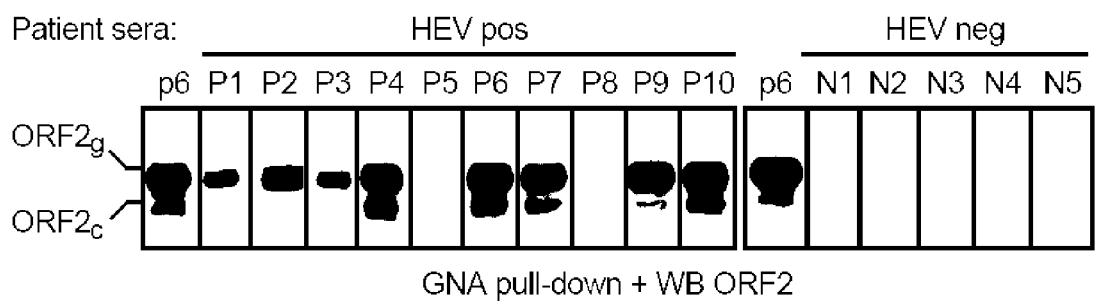
Figure 3B:
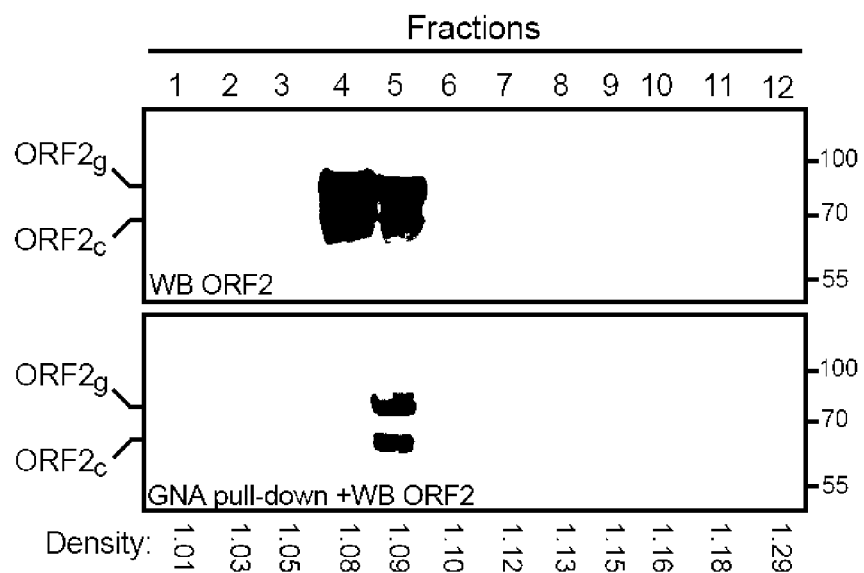

FIG. 3: ORF2g and ORF2c proteins are the major HEV antigens in infected patients. (A) GNA pull-down on patient sera followed by ORF2 probing. Pull-down of PLC3/HEV-p6 supernatant was used as a positive control. (B) Fractionation on iodixanol gradient (7.5-40%) of the P6 patient serum and analysis of the ORF2 content of each fraction by WB and GNA pull-down. (C) HEV RNA levels in each fraction measured by RT-qPCR. (D) Detection of HEV Ag in each gradient fraction using the Wantai HEV-Ag ELISA$^{Plus}$ kit. Results are expressed as signal to cut-off ratios (S/CO).

Figure 4:
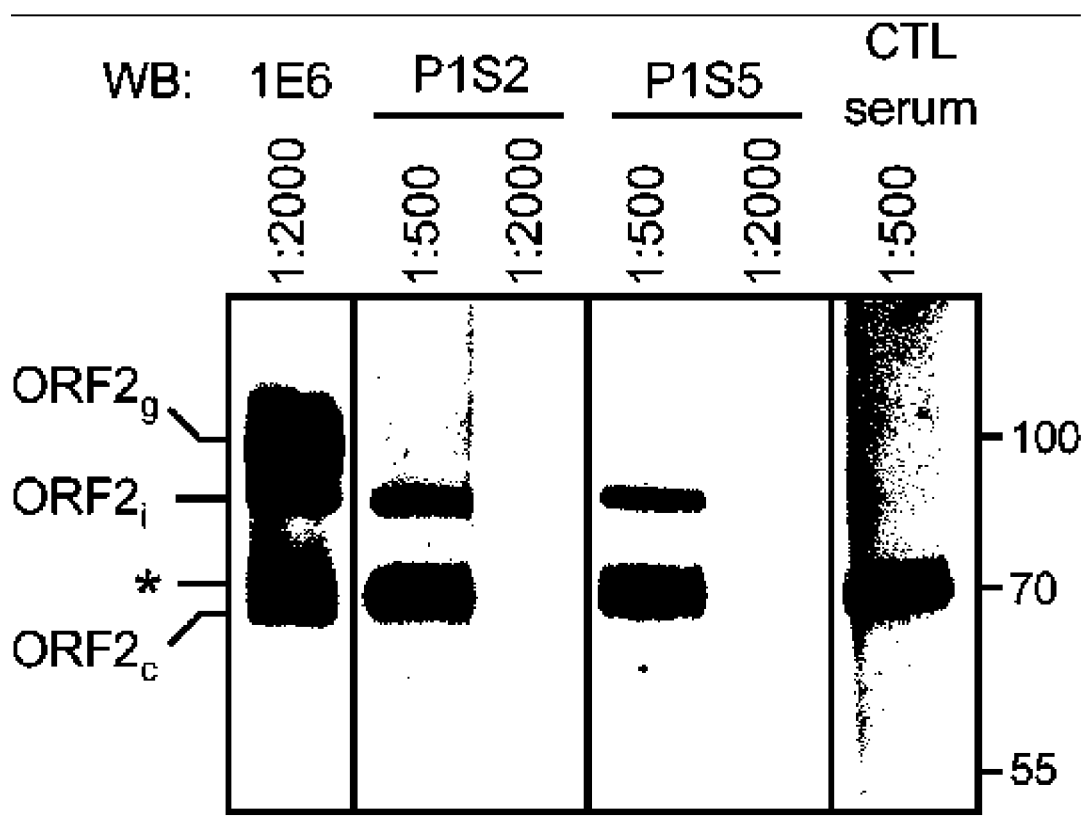

FIG. 4: Western blotting experiments showing antibodies specificity.

EXAMPLE 1

Materials and Methods
Chemicals and Cell Cultures.
PLC/PRF/5 (CRL-8024), PLC1, PLC3 and A549 (CCL-185) cells were grown in Dulbecco's modified Eagle's medium (DMEM) supplemented with 10% inactivated fetal calf serum (DMEM/FCS) at 37° C. Transfected cells were maintained at 32° C. in a medium containing DMEM/M199 (1v:1v), 1 mg/ml of lipid-rich albumin (Albumax I™) and 40 nM $Na_2SeO_3$.

Plasmids and Transfection.
Plasmids expressing the cell culture adapted gt3 Kernow C-1 strain (HEV-p6, GenBank accession number JQ679013) or the replicon expressing the *Gaussia* luciferase gene (HEV-p6GLuc) were provided by S.U Emerson[6]. The replication-deficient replicon HEV-p6GLucGAD was generated by mutating the GDD motif into the RNA-dependent RNA polymerase gene[7]. Capped RNA transcripts were generated with the mMESSAGE mMACHINE® kit (Ambion). Capped RNAs were delivered to cells by electroporation using a Gene Pulser Xcell™ apparatus (Bio-Rad).

Kinetics Experiments and Virus Production.
PLC1 and PLC3 cells were electroporated with capped HEV-p6 RNA (20 µg/4×10$^6$ cells). For kinetics experiments, every two days, supernatants were harvested and cells were lysed in buffer containing 50 mM TrisHCl (pH 7.5), 150 mM NaCl, 5 mM EDTA, 0.5% (v/v) NP40, 0.05% sodium deoxycholate, 1 mM PMSF and protease inhibitor cocktail (Complete; Roche). For virus production, cells were split every 10 days. Supernatants were collected and stored at −80° C.

Density Gradients.
PLC3/HEV-p6 supernatant was concentrated with a Vivaspin ultrafiltration spin column (Sartorius). Concentrated supernatant or patient serum (500 µl) was layered on a 7.5-40% iodixanol gradient, which was centrifuged at 160,000 g for 16 h at 4° C. Twelve fractions of 1 ml were collected and their density was measured by refractometry. The HEV RNA titer was determined by RT-qPCR. Each fraction was used to infect A549 cells. Infectivity was determined by indirect immunofluorescence, immunoblotting, and RNA and viral titration. For patient samples, fractions were used for ORF2 probing, GNA pull-down, and RNA quantification.

Purification of Infectious Particles on Iodixanol Cushion.
Supernatant of PLC3/HEV-p6 was concentrated by centrifugation through a 20% iodixanol cushion at 160,000 g for 4 h at 4° C. The cushion was resuspended in PBS, ultracentrifuged a second time, and the pellet was resuspended in PBS.

Infection of Humanized Mice.

Primary human hepatocytes were transplanted into homozygous uPA$^{+/+}$-SCID mice, as previously described[8]. Humanized mice were inoculated via intrasplenic route with HEV-p6 purified on iodixanol gradient (fraction6, F6p6, 8.7×10$^7$ IU/mouse) or with the same volume of fraction6 from a control gradient prepared with concentrated supernatant of non-transfected PLC3 cells (F6 control). Non-transplanted mice inoculated with these preparations served as negative controls. A chimeric mouse inoculated with a gt1 (Sar55, 2.8×10$^5$ IU/mouse) stool suspension was used as a positive control[9]. Stool and plasma samples were collected on a weekly basis. Viral RNA was detected and quantified in mouse plasma and stool using RT-qPCR, as described[9]. Sequencing of the S17 region was performed as described[9].

Transmission Electron Microscopy (TEM).

The formvar-carbon TEM grids (S162, Oxford Instruments) were either incubated with 0.01% poly-L-lysine for 30 min at room temperature (RT) or with poly-L-lysine and then with anti-ORF3 (Bioss antibodies), anti-ORF2 (1E6), or isotype-matched antibodies (20 m/ml) for 1 h at RT. Grids were washed in PBS and incubated for 2 h at RT with viral samples. TEM grids were washed in PBS and incubated for 20 min in 4% paraformaldehyde and 1% glutaraldehyde in 0.1M phosphate buffer, pH7.2. Particles trapped on grids were stained with 0.5% uranyl acetate before examination under a JEOL-1230 TEM. For delipidation, particles were either treated for 1 h at 37° C. with 1% sodium deoxycholic acid, 0.1% trypsin, then processed for TEM, or treated in the same conditions then layered on an iodixanol gradient. After determining density and RNA levels, fraction 11 was processed for TEM.

Glycosidase Digestions.

Protein samples were denatured for 10 min at 95° C. in glycoprotein denaturing buffer (New England Biolabs). Digestions with glycosidases were carried out for 4 h at 37° C. in the presence of 1% NP40 and the buffer provided by the manufacturer (NEB). Samples prepared in the same conditions but without glycosidase were used as controls.

GNA Pull-Down.

Agarose-conjugated GNA beads were incubated for 2 h at RT with 50-500 μl of patient serum or 100 μl of supernatant of PLC3/HEV-p6. Beads were washed 8 times with PBS 0.5% NP40. Proteins were eluted in Laemmli Buffer and analyzed by SDS-PAGE. Unconjugated agarose beads were used as a negative control.

Patient Samples.

Patient samples were collected in France between 2012 and 2017. This was a non-interventional study. Samples were obtained only via standard viral diagnostics following a physician's order (no supplemental or modified sampling). Data were analyzed anonymously. The French Public Health Law (CSP Art L 1121-1.1) does not require written informed consent from patients for such a protocol.

Detection of HEV-Ag.

Gradient fractions were diluted in PBS and Ag levels were measured with the Wantaï HEV-Ag ELISA$^{Plus}$ kit (Wantaï Biological Pharmacy Enterprise) according to the manufacturer's instructions.

Results:

Establishment of an Efficient HEV Cell Culture System

In an attempt to establish a cell culture system for HEV, we first analyzed HEV replication in two subclones of the PLC/PRF/5 cell line, namely PLC1 and PLC3 cells. We used the *Gaussia* luciferase (GLuc)-expressing HEV gt3 replicon named HEV-p6GLuc[6], in which the ORF2 coding sequence was replaced with the secreted GLuc sequence. Thus, the amount of secreted GLuc is proportional to viral RNA synthesis and consequently to HEV replication. PLC1, PLC3, and parental PLC/PRF/5 cells were electroporated with HEV-p6GLuc RNA or with a non-replicative HEV-p6GLuc genome (HEV-p6GLucGAD). The replication levels of HEV-p6GLuc steadily increased over time in the three cell lines (data not shown), but PLC1 and PLC3 cells showed higher HEV replication fold increase, as compared to PLC/PRF/5 cells. Experiments were thereafter conducted using PLC1 and PLC3 cells.

We assessed the ability of PLC1 and PLC3 cells to express viral proteins and produce infectious particles in kinetics experiments. PLC1 and PLC3 cells were electroporated with the HEV-p6 RNA strain[6]. Immunofluorescence with anti-ORF2 and anti-ORF3 antibodies showed that over 80% of cells expressed viral proteins (data not shown), indicating that PLC1 and PLC3 cells are highly transfectable, and that robust replication and expression of viral genome likely occur in these cells. It must be noted that ORF2 expression was inhibited in the presence of Sofosbuvir (SFV) (data not shown), confirming the specificity of the signal.

We next analyzed the expression of ORF2 and ORF3 proteins in the cell lysates and supernatants of HEV-p6 electroporated PLC1 and PLC3 cells by western blotting (WB) at different time points. Importantly, the ORF2 protein was detected in the cell lysates and supernatant of PLC1 cells as early as 2 and 4 days post-electroporation (p.e.), respectively (data not shown). In HEV-p6 electroporated PLC3 cells, expression of the ORF2 protein was slightly delayed. It must be noted that PLC3 cells grow more slowly than PLC1 cells, which could explain the observed differences. In addition to the major product of ORF2, ORF2-related proteins with lower molecular weights were also detected in cells and supernatants, indicating that the ORF2 capsid protein likely undergoes post-translational modifications. The ORF3 protein was also early detected at 2 and 4 days p.e. in PLC1 and PLC3 cell lysates, respectively (data not shown). In contrast, the ORF3 protein was faintly detected in the supernatants of electroporated cells, indicating that this protein is mainly expressed intracellularly.

The major ORF2 product in the supernatant (data not shown) displayed a higher apparent molecular weight than the intracellular form (data not shown), suggesting that the highly secreted ORF2 protein likely undergoes post-translational modifications. Comparison of intracellular and extracellular ORF3 proteins showed that the secreted ORF3 protein migrated slightly faster than the intracellular protein (data not shown) likely reflecting differences in protein phosphorylation[10] or undescribed modifications of the ORF3 protein.

Viral RNA and infectious particles were also monitored in the supernatants of transfected cells collected on different days p.e. HEV RNA levels were assessed by RT-qPCR. High RNA levels were detected as early as 2 days p.e. (data not shown). RNA titers increased progressively and reached 1.1×10$^8$ and 3.3×10$^7$ copies/ml at day 10 for PLC1 and PLC3 cells, respectively (data not shown). In parallel, infectious viral titers were determined and reached 7×10$^3$ and 1.5×10$^3$ ffu/ml for PLC1 and PLC3 cells, respectively. These results indicate that assembly of infectious viral particles occurs very early and equally in HEV-p6 electroporated PLC1 and PLC3 cells. However, HEV infectivity represents 1.5×10$^4$ RNA copies/ffu for PLC1 cells and 2.2×10$^4$ RNA copies/ffu for PLC3 cells, indicating that the assembly of infectious HEV particles is likely an inefficient process. However, we cannot exclude the possibility that a viral or cellular inhibitor blocks HEV infection and biases the infectious titers. Further experiments were carried out using PLC3 cells.

ORF2 Capsid Protein is Massively Produced but Only a Small Fraction is Assembled into Infectious Particles.

To produce large amounts of infectious supernatants, we cultured HEV-p6 transfected PLC3 cells during 47 days. Supernatants were pooled, concentrated, and fractionated on an iodixanol gradient. The distribution of ORF2 protein, ORF3 protein, RNA and infectious viral particles was analyzed from each fraction (data not shown). ORF2 protein was detected from fractions 2 to 7 but more abundantly in fractions 3 to 5 (data not shown). As observed in the supernatants of transfected cells (FIG. 1C), ORF2 protein in fractions 2 to 5 was detected as two products, one major product of approximately 90 kDa (ORF2g) and a smaller product of around 75 kDa (ORF2c). ORF2-related proteins with lower molecular weights were also detected at the top of the gradient in fractions 2 to 5, which might correspond to additional processed forms of the proteins. In contrast, the ORF2 protein was mainly detected as an 80 kDa product (ORF2i) in fractions 6 and 7, which corresponds to the size of intracellular ORF2 (FIG. 1C). The ORF3 protein was exclusively detected in fractions 5 to 7 but most abundantly in fraction 6 (data not shown). Interestingly, only one major peak of RNA was detected in fraction 6, with a density of 1.10 g/ml (data not shown). Therefore, a large amount of capsid protein (fractions 2 to 4) was not associated with the viral RNA while the ORF3 protein was.

The infectivity of each fraction was analyzed by infecting A549 cells. Expression of ORF2 and ORF3 proteins was analyzed by WB (data not shown) and indirect immunofluorescence (data not shown) five days post-infection. ORF2i and ORF3 proteins were detected in the lysates of cells infected with fractions 5, 6 and 7 (data not shown), suggesting that infectious particles were associated with these fractions. Indeed, immunofluorescence staining of A549 cells inoculated with fractions 5, 6 and 7 were positive for ORF2 protein expression whereas cells inoculated with fractions 1 to 4 and fractions 8 to 12 were negative (data not shown). Fraction 6 showed the highest infectious titer ($5\times10^6$ ffu/ml). While ORF2g and ORF2c proteins were detected in cells inoculated with fractions 3 and 4 (data not shown), no specific infection was observed with these fractions by immunofluorescence (data not shown), indicating that ORF2g and ORF2c are likely very stable proteins binding to the cell surface that can be detected after several days of incubation.

It must be noted that the exosomal CD81 tetraspanin was detected in infectious fractions (data not shown), supporting the hypothesis that HEV particles likely exploit the exosomal secretory pathway for their egress[11].

Together, our results indicate that during the HEV lifecycle, the ORF2 capsid protein is massively produced, but only a small fraction (ORF2i) is assembled into infectious particles that are secreted through the exosomal pathway.

Infection of Human Liver Chimeric Mice with HEVcc Particles.

Recently, human liver chimeric mice have been described as valuable models for studying in vivo chronic HEV infection and evaluating antiviral molecules[9,12-14]. Establishment of HEV infection in chimeric mice was achieved after inoculation of gt1 or gt3 virions. However, inoculation of mice with non-treated cell culture supernatant-derived particles did not result in robust infection. Therefore, we next evaluated whether our HEVcc particles were able to infect primary human hepatocyte (PHH)-transplanted mice[9]. Chimeric mice were inoculated via intrasplenic route with either fraction 6 of HEV-p6 (F6p6) purified on iodixanol gradient (FIG. 2) or fraction 6 of a control gradient prepared from non-transfected PLC3 cells supernatant (F6 control, neg 1) (data not shown). A human chimeric mouse inoculated with a gt1 stool suspension (Sar55) was used as a positive control[9]. A non-transplanted mouse inoculated with F6p6 was used as a second negative control (neg 2). While to a lesser extent than the gt1-infected mouse, the F6p6-inoculated chimeric mouse still showed signs of active infection (data not shown). Indeed, HEV RNA was detected in stools of F6p6-inoculated chimeric mouse from week 2 to 10 with a significant increase from week 8 to 10 (data not shown). Genomic HEV RNA was also detected in mouse liver (data not shown) and small intestine content (data not shown). RNA load in the F6p6-inoculated mouse increased more slowly as compared to the gt1-inoculated mouse, as previously described[9] but for the first time, we demonstrate a robust infection of a chimeric mouse inoculated with HEV particles derived from cell culture supernatant.

Since HEV-p6 strain contains the human S17 ribosomal protein fragment that confers a growth advantage[6,15], we next sequenced this region of HEV-p6 from the F6p6-infected mouse (stool week 9 p.i. and one liver piece) and compared it to the inoculum. We did not find any reversion of adaptive mutations in the S17 region (data not shown).

Ultrastructure of HEV Particles.

Recently, a new strategy based on the direct specific immunocapture (IC) of hepatitis C virus (HCV) particles on transmission electron microscopy (TEM) grids led, for the first time, to the precise description of their ultrastructure[16]. To define the morphology of HEVcc particles, which has never been precisely described, we used the same approach on isolated infectious particles. We first analyzed material captured on grids coated with poly-L lysine, a polycationic attachment factor. We observed a fairly homogeneous population of particles of 40-70 nm in size (data not shown). We next performed IC with an antibody specific to the ORF3 protein that had been described as exposed on lipid-associated HEV particles. We observed particles with an apparent internal icosahedral substructure likely corresponding to the capsid (data not shown). The calculation of size distribution showed that particle sizes ranged from 40 nm to 70 nm. In contrast, no particles were observed when an anti-ORF2 (1E6) (data not shown) or isotype control antibodies (data not shown) were used. However, when viral preparation was first partially delipidated by sodium deoxycholate and trypsin (DT) treatment before IC with the anti-ORF2 antibody, two populations of particles were immunocaptured: a major population consisting of particles of 30-50 nm in size and a more heterogeneous population with particles of 90-140 nm (data not shown). Thus, DT treatment unmasked the 1E6 epitope on viral particles and led to IC of small HEV particles that likely correspond to naked virions. However, DT treatment did not fully remove ORF3 and associated lipids since some particles were still captured by an anti-ORF3 antibody (data not shown). The larger size of these particles is likely due to dissociation of their lipid coats. In contrast, when DT-treated particles were purified on density gradient before IC (data not shown), a highly homogeneous population of particles of approximately 32 nm was immunocaptured with 1E6 while no particles were captured by IC anti-ORF3. These particles, with a density of 1.18 g/ml, displayed an icosahedral structure likely corresponding to naked capsids.

We next analyzed the ultrastructure of authentic particles from three HEV-infected patient sera (HEVser). As for HEVcc, no particles were observed by IC anti-ORF2 or IC with irrelevant antibodies (data not shown). In contrast, IC anti-ORF3 resulted in the efficient isolation of pleomorphic populations. HEVser1 and HEVserST-1 particles had a similar morphology to HEVcc particles while HEVser2 particles displayed a thick outer layer likely corresponding to lipids (data not shown). The calculation of size distribution of immunocaptured particles showed that the mean and median diameters of HEVser particles were generally larger than those of HEVcc particles and differed between patients (data not shown). Particles from HEVser2 were the largest with a mean diameter of 120 nm. These results indicate that the lipid content of particles likely determine particle size, as described for HCV particles[16].

Lastly, we analyzed the ultrastructure of particles from an HEV-infected patient stool, as described above. In contrast to HEVcc and HEVser, stool particles were captured by IC anti-ORF2, whereas no particles were captured by IC anti-ORF3 (data not shown). Although particles appeared to be entangled in impurities limiting calculation of size distribution, the mean diameter of HEV stool particles was 28 nm (n=34, mean=28 nm, median=28 nm, SD=4 nm), which is in accordance with previous observations[17]. As for delipidated HEVcc, stool particles displayed an icosahedral structure likely corresponding to naked capsids.

Characterization of the Different Forms of ORF2 Protein.

We developed a purification system using a 20% iodixanol cushion to easily separate infectious particles (ORF2i, FIG. 1A, Pellet) from ORF2g/ORF2c proteins that are not associated with infectious particles (FIG. 1A, Top).

HEV produces large amounts of secreted ORF2g/ORF2c proteins that are likely glycosylated/processed forms of the ORF2 protein. In contrast, infectious particle-associated ORF2 protein (ORF2i) purified by iodixanol gradient (F6p6) or cushion (Pellet/Cushion) displayed the same size as intracellular ORF2 protein (Cells) (FIG. 1B), indicating that ORF2i likely does not undergo post-translational modifications.

Since the ORF2 protein sequence contains three potential sites for N-linked glycosylation and multiple sites for O-linked glycosylation, we next analyzed the sensitivity of ORF2 proteins to treatment with different glycosidases (FIG. 1C). Endoglycosidase H (EndoH) cleaves within the chitobiose core of high mannose and some hybrid oligosaccharides from N-glycoproteins. Peptide-N-Glycosidase F (PNGaseF) cleaves between the innermost N-acetyl glucosamine and asparagine residues of high mannose, hybrid and complex oligosaccharides from N-glycoproteins. O-Glycosidase (O-Gly) catalyzes the removal of some O-linked disaccharides. Neuraminidase (Neura) catalyzes the hydrolysis of sialic acid residues from N- and O-glycoproteins. It should be noted that terminal sialic acids block the action of O-Gly. The ORF2i protein expressed from cell lysates or purified HEV particles was resistant to glycosidase digestions (FIG. 1C), indicating that this protein is not N- or O-glycosylated. In contrast, secreted ORF2g/ORF2c proteins were sensitive to digestion with EndoH and PNGaseF glycosidases, as attested by the mobility shift upon treatment, indicating that these proteins are N-glycoproteins. ORF2g/ORF2c proteins were resistant to O-Gly treatment but sensitive to treatment with Neura and more markedly to a combination of Neura and O-Gly. These results indicate that ORF2g/ORF2c proteins are sialylated and O-glycosylated proteins. Importantly, ORF2g/ORF2c proteins were precipitated by a *Galanthus nivalis* Agglutinin (GNA) pull-down, a lectin that interacts with high-mannose-type glycans confirming the oligomannosidic nature of ORF2g/ORF2c N-glycans (FIG. 1D) and allowing the easy and specific precipitation of ORF2g/ORF2c proteins.

We demonstrated that secreted ORF2g/ORF2c are glycosylated proteins, indicating that these proteins go through the secretory pathway. However, ORF2g/ORF2c proteins were not detected at the intracellular level. We therefore hypothesized that ORF2g/ORF2c proteins might move rapidly through the secretory pathway and be secreted quickly without intracellular accumulation. We thus treated HEV-p6 expressing PLC3 cells with Brefeldin A (BFA), a protein secretion inhibitor[18] (FIG. 1E). Upon BFA treatment, secretion of ORF2g/ORF2c proteins was blocked. Interestingly, a diffuse band likely corresponding to ORF2g and a faint band likely corresponding to ORF2c were detected in the lysate of BFA-treated cells, indicating that upon protein secretion blocking, ORF2g/ORF2c proteins accumulate in the cell, thus validating our hypothesis.

Figure 2B:
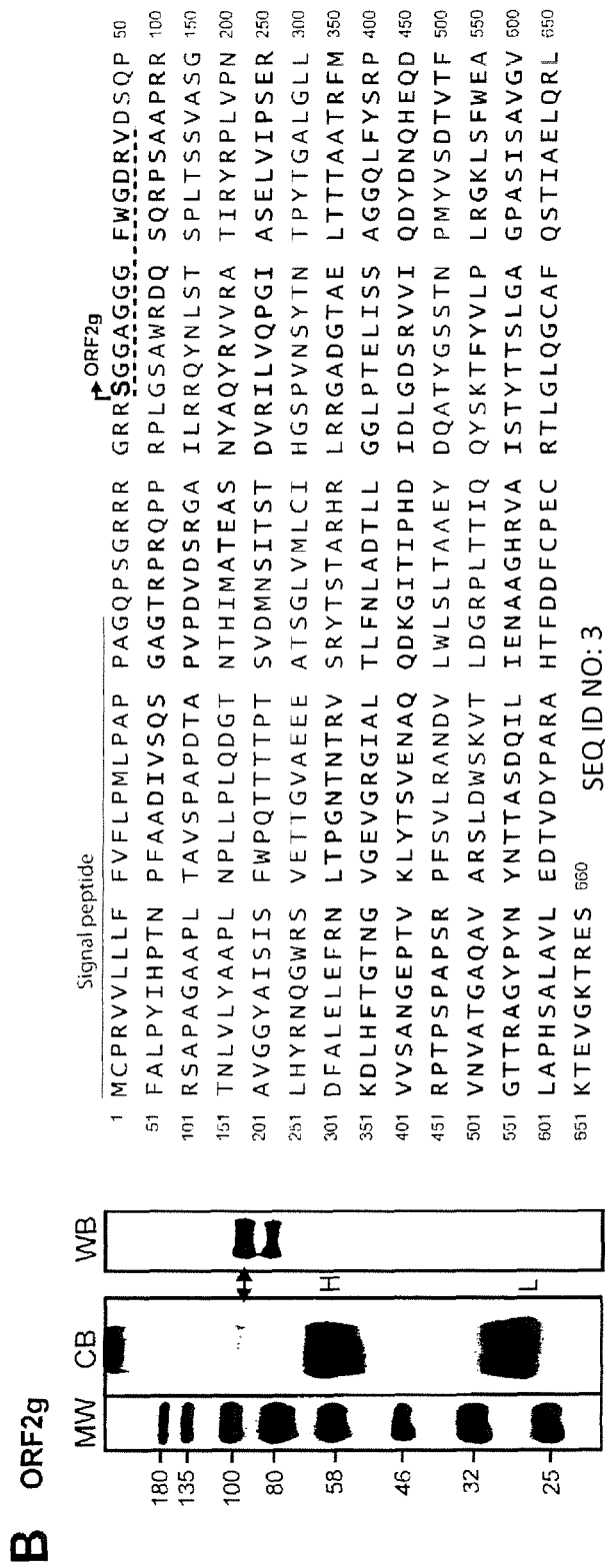
Figure 2C:
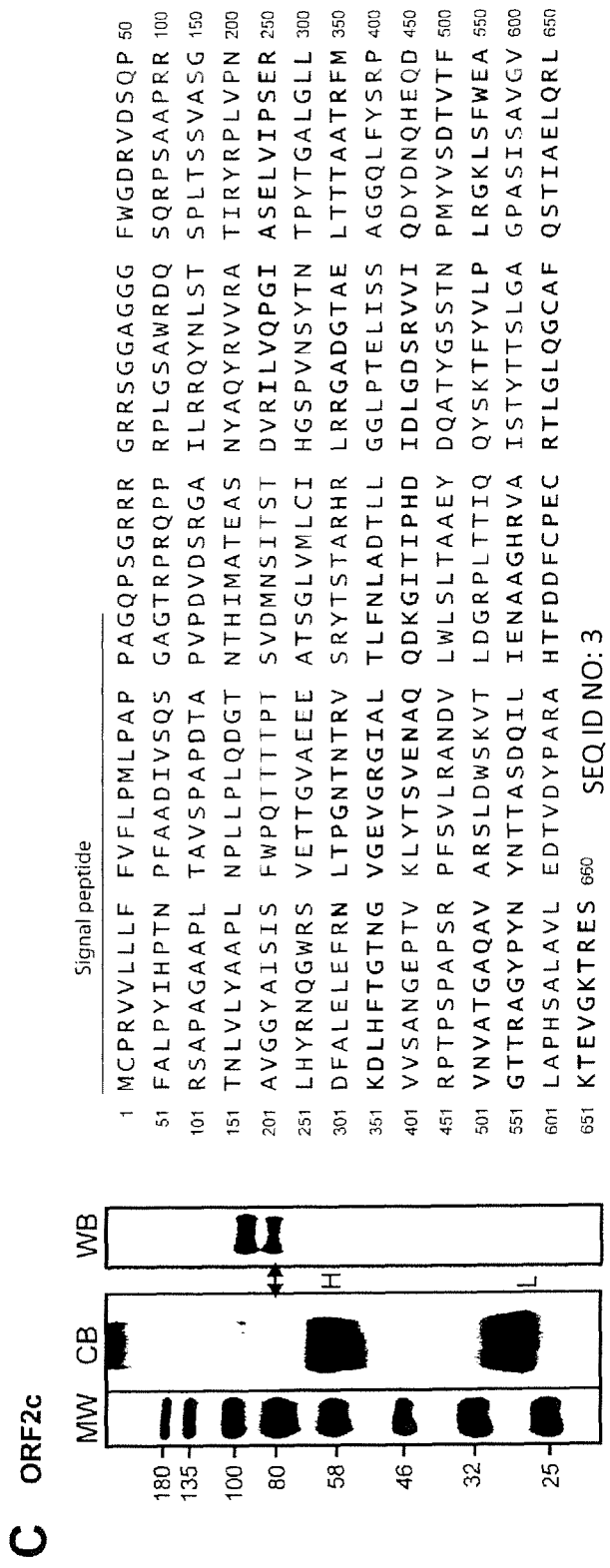

We next analyzed the sequence of ORF2 proteins by mass spectrometry. Viral particles purified on iodixanol cushion and ORF2g/ORF2c proteins immunoprecipitated with an anti-ORF2 antibody (4B2) were resolved by SDS-PAGE. The Colloidal blue stained bands corresponding to ORF2i, ORF2g and ORF2c in WB (FIG. 2) were digested in-gel with trypsin or AspN and then analyzed by nanoLC-MS/MS. Identified peptides and sequence covering are shown in FIG. 2. For the three proteins, the C-terminal end was fully covered, demonstrating the absence of processing at their C-termini. For ORF2i protein, a semi-tryptic peptide covering half of the signal peptide (SP) was unexpectedly identified (FIG. 2A, dashed line), suggesting that the SP of ORF2i might not be cleaved. For ORF2g, tryptic and semi-AspN peptides starting with $Ser^{34}$ were identified, suggesting that the first aa of the ORF2g protein might correspond to $Ser^{34}$ (FIG. 2B). For ORF2c, tryptic peptides starting with $Iso^{234}$ were identified, suggesting that the first aa of the ORF2c protein might correspond to one of the aa in proximity to $Iso^{234}$ (FIG. 2C). Since semi-tryptic and semi-AspN peptides correspond to either natural protein processing or non-specific proteolytic events during proteomics analyses, we further performed labeling with N-succinimidyloxycarbonylmethyl tris (2,4,6-trimethoxyphenyl) phosphonium bromide (TMPP-Ac-OSu), which binds specifically to the N-terminus of intact proteins[19]. Peptides identified with TMPP-Ac-OSu modification confirmed that the first aa of ORF2i and ORF2g corresponds to $Leu^{14}$ and $Ser^{34}$, respectively (FIGS. 1F, 2). In contrast, as TMPP-Ac-OSu labeling did not identify the first aa of ORF2c, further studies are necessary to clarify this observation. Together, these data indicate that the ORF2g protein loses its SP and is likely processed by secretory pathway proteases. In contrast, the ORF2i protein is not processed by a signal peptidase and therefore likely not translocated into the ER lumen.

ORF2g/ORF2c Proteins are the Major Antigens in HEV-Infected Patient Sera

Figures 3C, 3D:
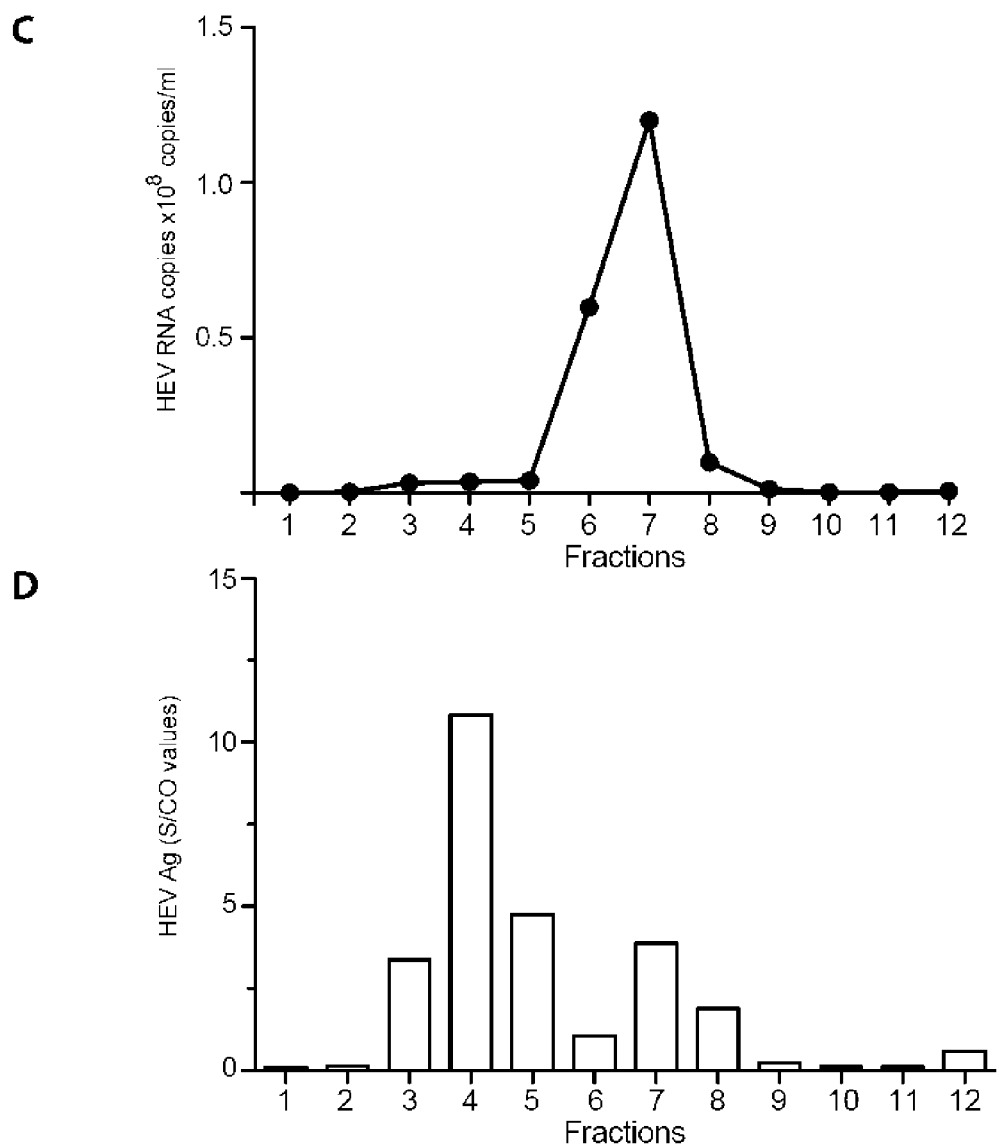

Since we demonstrated that in cell culture, HEV mainly produces glycosylated forms of ORF2 proteins that are not associated with infectious particles, we next sought to determine whether the same occurs in infected patients. Sera from 17 infected HEV patients and from five HEV-negative patients were precipitated by GNA pull-down and probed for the ORF2 protein (FIG. 3A), as described above. GNA-pulldown of PLC3/HEV-p6 supernatant was used as a positive control. Strikingly, 13 and 7 out of 17 HEV-positive sera displayed large amounts of the ORF2g and ORF2c proteins, respectively. ORF2 proteins were not detected in HEV-negative sera. In addition, the detection of ORF2g/ORF2c proteins was dependent neither on the patient's HEV strain nor on the serum viral load (Table 1). Importantly, fractionation of a patient serum (P6 patient) on an iodixanol gradient followed by GNA pull-down of each fraction (FIG. 3B) demonstrated that, as in cell culture, very large amounts of ORF2g/ORF2c proteins were isolated in light fractions (fractions 4 and 5) and pull-down by GNA. However, these fractions were not associated with infectious material, since they were not associated with the viral genome (FIG. 3C). It should be noted that the ORF2 proteins present in fraction 4 were likely not precipitated by GNA beads due to the presence of high amounts of human albumin. Our results indicate that ORF2g/ORF2c proteins are likely the major antigens in HEV-infected patient sera. Therefore, we quantified ORF2 proteins in each fraction of the gradient with the Wantaï HEV-antigen ELISA$^{Plus}$ assay (FIG. 3D). Interestingly, the highest amount of antigen was detected in fraction 4, containing the ORF2g/ORF2c proteins, whereas lower amounts of antigens were detected in the other fractions and notably in fraction 7, the infectious fraction. Together, our results indicate that in infected patients, HEV produces high amounts of glycosylated antigen protein that are not associated with infectious particles and might lead to a bias in diagnosis of active HEV infection.

TABLE 1

Features of HEV patient sera used in GNA pull-down

| Patients | Genotype | Serum titer $^a$ | Amount used in GNA pull-down $^b$ | Ag levels $^c$ | ORF2 proteins $^d$ |
|---|---|---|---|---|---|
| P1 | 3c | $1.3 \times 10^8$ | $6.5 \times 10^6$ | 17.4 | ORF2g |
| P2 | 3c | $3.7 \times 10^7$ | $1.8 \times 10^6$ | 19.4 | ORF2g |
| P3 | 3c | $2.1 \times 10^7$ | $2.1 \times 10^6$ | 17.4 | ORF2g |
| P4 | ND | $2.0 \times 10^5$ | $1.0 \times 10^5$ | 20.2 | ORF2g/ORF2c |
| P5 | 3f | $7.0 \times 10^5$ | $3.5 \times 10^5$ | ND | — |
| P6 | 3c | $1.6 \times 10^8$ | $1.6 \times 10^7$ | 19.4 | ORF2g/ORF2c |
| P7 | 3c | $1.2 \times 10^7$ | $1.2 \times 10^6$ | 18.6 | ORF2g/ORF2c |
| P8 | 3f | $1.2 \times 10^5$ | $0.6 \times 10^5$ | 5 | — |
| P9 | 3f | $1.5 \times 10^5$ | $0.7 \times 10^5$ | 19.7 | ORF2g/ORF2c |
| P10 | 3f | $1.2 \times 10^6$ | $0.6 \times 10^6$ | 18.9 | ORF2g/ORF2c |
| P11 | ND | ND | ND | 18.3 | ORF2g/ORF2c |
| P12 | 3f | $2.0 \times 10^6$ | $1.0 \times 10^6$ | ND | ORF2g |
| P13 | 3f | $2.1 \times 10^6$ | $1.0 \times 10^6$ | ND | ORF2g |
| P14 | 3e | $1.0 \times 10^6$ | $2.0 \times 10^5$ | ND | — |
| P15 | 3 | $1.1 \times 10^6$ | $2.0 \times 10^5$ | ND | — |
| P16 | 3c | ND | ND | ND | ORF2g |
| P17 | 3c | ND | ND | ND | ORF2g/ORF2c |

$^a$ in HEV RNA copies/ml
$^b$ in HEV RNA copies
$^c$ in S/CO values. Samples were diluted 100 times in PBS and quantified with the Wantaï HEV-Ag-ELISA kit.
$^d$ detected in GNA pull-down + WB anti-ORF2

Discussion:

By combining the highly replicative and cell culture-adapted p6 strain[6] and highly transfectable subclones of PLC/PRF/5 cells, we developed a new cell culture system for which viral replication and protein expression were detected very early post-transfection. Time-course experiments showed that the ORF2 protein was early and massively secreted into the supernatant of transfected cells, as recently reported[20,21]. Interestingly, ORF2 and ORF3 proteins migrated differently when detected either in cell lysate or supernatant, indicating that these proteins likely undergo post-translational modifications during their secretion. Further experiments would be necessary to identify such modifications in the ORF3 protein. The ORF2 protein contains three potential sites for N-linked glycosylation and multiple sites for O-linked glycosylation. Using expression vectors, it has been previously shown that the ORF2 protein is glycosylated and expressed on the cell surface[22-24], but it is not clear whether the glycosylated ORF2 protein is the natural form of the virion. Recently, it has been suggested that the HEV virion capsid is likely glycosylated[20], although Graff et al. showed the opposite[25]. Our study revealed that HEV produces large amounts of ORF2 proteins, named ORF2g and ORF2c, that are secreted, sialylated, N- and O-glycosylated but are not associated with infectious virions. A large portion of ORF2 proteins is likely translocated into the ER lumen where they are N-glycosylated and likely processed by proteases to generate ORF2g and ORF2c proteins. These two proteins move rapidly through the secretory pathway where they are O-glycosylated and sialylated, then quickly secreted. Interestingly, the presence of RGRR residues upstream of the ORF2g N-terminus suggests that a furin-like protease might be involved in its maturation. Further experiments would be necessary to characterize glycosylation and processing sites in the ORF2 sequence, notably the mechanism leading to the production of the ORF2c protein. In contrast, the ORF2i protein seen on an intracellular level and in virions is likely not translocated into the ER lumen and stays in the cytosolic compartment. Our results suggest the existence of two production pathways for the HEV capsid protein: (i) a major non-productive pathway in which ORF2 proteins are delivered to the secretion route where they are processed and quickly secreted. (ii) a productive pathway in which cytosolic ORF2 proteins are delivered to the virion assembly sites. Further studies are needed to thoroughly investigate these pathways.

In contrast to previous studies[9,13], we succeeded in infecting chimeric mice with gt3 HEVcc particles. The separation of infectious particles from ORF2g/ORF2c proteins by density gradient might explain our success, as these proteins interfere with the capacity of virions to infect target cells, using a mechanism which needs to be elucidated.

We found that during its lifecycle, HEV highly secretes glycosylated forms of the ORF2 protein, which circulate in infected patients and are the major antigens in patient sera. It would be interesting to define which form of ORF2 protein is recognized by antibodies from patients that have resolved their infections. HEV may produce ORF2g/ORF2c proteins as immunological bait. Interestingly, using TEM analyses, we found that ORF2g/ORF2c proteins do not form particulate material (data not shown) in contrast to other viruses such as hepatitis B virus, where the surface antigen forms subviral particles.

Our TEM analyses showed that HEVcc are particles of 40-70 nm in size displaying internal structures and the ORF3 protein at their surface. DT treatment and ultracentrifugation uncloaked small icosahedral capsids similar to those found in patient stools ([17] and our study), indicating that HEVcc are associated with lipids in which ORF3 is embedded. Our analyses showed that, although much larger, HEVser particles have a morphology similar to HEVcc particles. HEVser virions display the ORF3 protein at their surface and are likely highly associated with lipids. As HEVser diameters differed between patients, it would be interesting to determine if the observed size variations are related to lipid content, as recently demonstrated for HCV particles[16].

Recently, the Wantaï HEV-Ag-ELISA assay was marketed for diagnosing HEV infection. Comparative studies of this assay showed high levels of specificity and sensitivity 26-29. However, some discrepancies between antigen detection and RNA quantification were found in some samples in which the HEV antigen was detected in the absence of detectable RNA[27-29]. In our hands, the antigen assay was also very sensitive. However, we found that ORF2g/ORF2c proteins, which are not associated with infectious virions, were the main antigens recognized by the kit. Together, these data indicate that the results obtained with the HEV-Ag-ELISA assay must be cautiously interpreted. Indeed, this assay might not necessarily detect an active infection, since ORF2g/ORF2c proteins seem to be very stable in cell culture but likely also in patient sera[28], suggesting that these proteins might remain in patient sera even when HEV is no longer replicating in the liver.

EXAMPLE 2

Generation of Specific Antibodies Directed Against the ORF2i Protein.

A peptide (P1) that derives from the polypeptide of the present invention (ORF2i) was synthetised and coupled to KLH. Five mice were immunized three times at three weeks intervals with the P1 peptide. Freund's complete and incomplete adjuvants were used during immunisation. The animals were immunized by subcutaneous and intraperitoneal routes. Ten days after the third immunisation, mice have been bleeded and their sera tested for immunoreactivity. Sera were first assayed by indirect ELISA on plates coated with the P1 peptide (data not shown). Their specificity was next analyzed in western blotting experiments with a mixture of ORF2 proteins (ORF2i and ORF2g/ORF2c) as antigens (FIG. 4). Two (P1S2 and P1S5) out of five sera showed a highly specific recognition of the ORF2i protein, with no cross-reaction with the ORF2g/c proteins, as compared to the 1E6 antibody that recognizes the three forms (FIG. 4). Cloning and production of monoclonal antibodies are ongoing.

These results indicate that antibodies specifically directed against the ORF2i polypeptide can be produced. Such antibodies will be very suitable for determining presence of infectious particles of hepatitis E virus in a sample. More particularly, detection of the ORF2i or ORF2g polypeptide of the present invention is suitable for diagnosing hepatitis E virus infection in a subject.

REFERENCES

Throughout this application, various references describe the state of the art to which this invention pertains. The disclosures of these references are hereby incorporated by reference into the present disclosure.
1. Debing Y, Moradpour D, Neyts J, et al. Update on hepatitis E virology: Implications for clinical practice. Journal of Hepatology 2016; 65:200-212.
2. Pischke S, Hartl J, Pas S D, et al. Hepatitis E virus: Infection beyond the liver? Journal of Hepatology 2017; 66:1082-1095.
3. Khuroo M S, Khuroo M S. Hepatitis E: an emerging global disease—from discovery towards control and cure. Journal of Viral Hepatitis 2016; 23:68-79.
4. Feng Z, Hensley L, McKnight K L, et al. A pathogenic picornavirus acquires an envelope by hijacking cellular membranes. Nature 2013; 496:367-371.
5. Okamoto H. Culture systems for hepatitis E virus. J Gastroenterol 2012; 48:147-158.
6. Shukla P, Nguyen H T, Faulk K, et al. Adaptation of a genotype 3 hepatitis E virus to efficient growth in cell culture depends on an inserted human gene segment acquired by recombination. J Virol 2012; 86:5697-5707.
7. Emerson S U, Nguyen H, Graff J, et al. In vitro replication of hepatitis E virus (HEV) genomes and of an HEV replicon expressing green fluorescent protein. J Virol 2004; 78:4838-4846.
8. Meuleman P, Libbrecht L, De Vos R, et al. Morphological and biochemical characterization of a human liver in a uPA-SCID mouse chimera. Hepatology 2005; 41:847-856.
9. Sayed I M, Verhoye L, Cocquerel L, et al. Study of hepatitis E virus infection of genotype 1 and 3 in mice with humanised liver. Gut 2017; 66:920-929.
10. Zafrullah M, Ozdener M H, Panda S K, et al. The ORF3 protein of hepatitis E virus is a phosphoprotein that associates with the cytoskeleton. J Virol 1997; 71:9045-9053.
11. Nagashima S, Jirintai S, Takahashi M, et al. Hepatitis E virus egress depends on the exosomal pathway, with secretory exosomes derived from multivesicular bodies. Journal of General Virology 2014; 95:2166-2175.
12. Allweiss L, Gass S, Giersch K, et al. Human liver chimeric mice as a new model of chronic hepatitis E virus infection and preclinical drug evaluation. Journal of Hepatology 2016; 64:1033-1040.
13. van de Garde M D B, Pas S D, van der Net G, et al. Hepatitis E Virus (HEV) Genotype 3 Infection of Human Liver Chimeric Mice as a Model for Chronic HEV Infection. J Virol 2016; 90:4394-4401.
14. Sayed I M, Foquet L, Verhoye L, et al. Antiviral Research. Antiviral Research 2017; 141:150-154.
15. Shukla P, Nguyen H T, Torian U, et al. Cross-species infections of cultured cells by hepatitis E virus and discovery of an infectious virus-host recombinant. Proc. Natl. Acad. Sci. U.S.A. 2011; 108:2438-2443.
16. Piver E, Boyer A, Gaillard J, et al. Ultrastructural organisation of HCV from the bloodstream of infected patients revealed by electron microscopy after specific immunocapture. Gut 2016.
17. Balayan M S, Andjaparidze A G, Savinskaya S S, et al. Evidence for a virus in non-A, non-B hepatitis transmitted via the fecal-oral route. Intervirology 1983; 20:23-31.
18. Klausner R D, Donaldson J G, Lippincott-Schwartz J. Brefeldin A: insights into the control of membrane traffic and organelle structure. J Cell Biol 1992; 116:1071-1080.
19. Gallien S, Perrodou E, Carapito C, et al. Ortho-proteogenomics: Multiple proteomes investigation through orthology and a new M S-based protocol. Genome Research 2008; 19:128-135.
20. Qi Y, Zhang F, Zhang L, et al. Hepatitis E Virus Produced from Cell Culture Has a Lipid Envelope. PLoS ONE 2015; 10:e0132503.
21. Shiota T, Li T C, Yoshizaki S, et al. Establishment of hepatitis E virus infection-permissive and -non-permissive human hepatoma PLC/PRF/5 subclones. Microbiol. Immunol. 2015; 59:89-94.
22. Jameel S, Zafrullah M, Ozdener M H, et al. Expression in animal cells and characterization of the hepatitis E virus structural proteins. J Virol 1996; 70:207-216.
23. Torresi J, Meanger J, Lambert P, et al. High level expression of the capsid protein of hepatitis E virus in diverse eukaryotic cells using the Semliki Forest virus replicon. J. Virol. Methods 1997; 69:81-91.

24. Zafrullah M, Ozdener M H, Kumar R, et al. Mutational analysis of glycosylation, membrane translocation, and cell surface expression of the hepatitis E virus ORF2 protein. J Virol 1999; 73:4074-4082.
25. Graff J, Zhou Y-H, Torian U, et al. Mutations within potential glycosylation sites in the capsid protein of hepatitis E virus prevent the formation of infectious virus particles. J Virol 2008; 82:1185-1194.
26. Trémeaux P, Lhomme S, Chapuy-Regaud S, et al. Performance of an antigen assay for diagnosing acute hepatitis E virus genotype 3 infection. J. Clin. Virol. 2016; 79:1-5.
27. Zhao C, Geng Y, Harrison T J, et al. Evaluation of an antigen-capture EIA for the diagnosis of hepatitis E virus infection. Journal of Viral Hepatitis 2015; 22:957-963.
28. Behrendt P, Bremer B, Todt D, et al. Hepatitis E Virus (HEV) ORF2 Antigen Levels Differentiate Between Acute and Chronic HEV Infection. Journal of Infectious Diseases 2016; 214:361-368.
29. Geng Y, Zhao C, Huang W, et al. Detection and assessment of infectivity of hepatitis E virus in urine. Journal of Hepatology 2016; 64:37-43.

We claim:

1. An ORF2i polypeptide consisting of an amino acid sequence as set forth in SEQ ID NO:1; or an ORF2g polypeptide consisting of an amino acid sequence as set forth in SEQ ID NO:2, wherein the ORF2i polypeptide or the ORF2g polypeptide is coupled to keyhole limpet hemocyanin (KLH).

2. The ORF2i polypeptide of claim 1, which is not glycosylated.

3. The ORF2g polypeptide of claim 1, which is glycosylated.

4. A nucleic acid molecule encoding for an ORF2i polypeptide consisting of the sequence set forth by SEQ ID NO: 1 or an ORF2g polypeptide consisting of the sequence set forth by SEQ ID NO: 2.

5. The nucleic acid molecule of claim 4, wherein the nucleic acid molecule is present in a vector.

* * * * *

SEQUENCE LISTING

<160> NUMBER OF SEQ ID NOS: 3

<210> SEQ ID NO 1
<211> LENGTH: 647
<212> TYPE: PRT
<213> ORGANISM: Hepatitis E virus

<400> SEQUENCE: 1

```
Leu Pro Met Leu Pro Ala Pro Ala Gly Gln Pro Ser Gly Arg Arg
1               5                   10                  15

Arg Gly Arg Arg Ser Gly Gly Ala Gly Gly Gly Phe Trp Gly Asp Arg
                20                  25                  30

Val Asp Ser Gln Pro Phe Ala Leu Pro Tyr Ile His Pro Thr Asn Pro
                35                  40                  45

Phe Ala Ala Asp Ile Val Ser Gln Ser Gly Ala Gly Thr Arg Pro Arg
            50                  55                  60

Gln Pro Pro Arg Pro Leu Gly Ser Ala Trp Arg Asp Gln Ser Gln Arg
65                  70                  75                  80

Pro Ser Ala Ala Pro Arg Arg Arg Ser Ala Pro Ala Gly Ala Ala Pro
                85                  90                  95

Leu Thr Ala Val Ser Pro Ala Pro Asp Thr Ala Pro Val Pro Asp Val
                100                 105                 110

Asp Ser Arg Gly Ala Ile Leu Arg Arg Gln Tyr Asn Leu Ser Thr Ser
            115                 120                 125

Pro Leu Thr Ser Ser Val Ala Ser Gly Thr Asn Leu Val Leu Tyr Ala
    130                 135                 140

Ala Pro Leu Asn Pro Leu Leu Pro Leu Gln Asp Gly Thr Asn Thr His
145                 150                 155                 160

Ile Met Ala Thr Glu Ala Ser Asn Tyr Ala Gln Tyr Arg Val Val Arg
                165                 170                 175

Ala Thr Ile Arg Tyr Arg Pro Leu Val Pro Asn Ala Val Gly Gly Tyr
            180                 185                 190

Ala Ile Ser Ile Ser Phe Trp Pro Gln Thr Thr Thr Thr Pro Thr Ser
        195                 200                 205

Val Asp Met Asn Ser Ile Thr Ser Thr Asp Val Arg Ile Leu Val Gln
    210                 215                 220

Pro Gly Ile Ala Ser Glu Leu Val Ile Pro Ser Glu Arg Leu His Tyr
225                 230                 235                 240

Arg Asn Gln Gly Trp Arg Ser Val Glu Thr Thr Gly Val Ala Glu Glu
                245                 250                 255

Glu Ala Thr Ser Gly Leu Val Met Leu Cys Ile His Gly Ser Pro Val
            260                 265                 270

Asn Ser Tyr Thr Asn Thr Pro Tyr Thr Gly Ala Leu Gly Leu Leu Asp
        275                 280                 285
```

Phe Ala Leu Glu Leu Glu Phe Arg Asn Leu Thr Pro Gly Asn Thr Asn
            290                 295                 300

Thr Arg Val Ser Arg Tyr Thr Ser Thr Ala Arg His Arg Leu Arg Arg
305                 310                 315                 320

Gly Ala Asp Gly Thr Ala Glu Leu Thr Thr Thr Ala Ala Thr Arg Phe
                325                 330                 335

Met Lys Asp Leu His Phe Thr Gly Thr Asn Gly Val Gly Glu Val Gly
            340                 345                 350

Arg Gly Ile Ala Leu Thr Leu Phe Asn Leu Ala Asp Thr Leu Leu Gly
                355                 360                 365

Gly Leu Pro Thr Glu Leu Ile Ser Ser Ala Gly Gln Leu Phe Tyr
370                 375                 380

Ser Arg Pro Val Val Ser Ala Asn Gly Glu Pro Thr Val Lys Leu Tyr
385                 390                 395                 400

Thr Ser Val Glu Asn Ala Gln Gln Asp Lys Gly Ile Thr Ile Pro His
                405                 410                 415

Asp Ile Asp Leu Gly Asp Ser Arg Val Val Ile Gln Asp Tyr Asp Asn
                420                 425                 430

Gln His Glu Gln Asp Arg Pro Thr Pro Ser Pro Ala Pro Ser Arg Pro
            435                 440                 445

Phe Ser Val Leu Arg Ala Asn Asp Val Leu Trp Leu Ser Leu Thr Ala
450                 455                 460

Ala Glu Tyr Asp Gln Ala Thr Tyr Gly Ser Ser Thr Asn Pro Met Tyr
465                 470                 475                 480

Val Ser Asp Thr Val Thr Phe Val Asn Val Ala Thr Gly Ala Gln Ala
                485                 490                 495

Val Ala Arg Ser Leu Asp Trp Ser Lys Val Thr Leu Asp Gly Arg Pro
            500                 505                 510

Leu Thr Thr Ile Gln Gln Tyr Ser Lys Thr Phe Tyr Val Leu Pro Leu
            515                 520                 525

Arg Gly Lys Leu Ser Phe Trp Glu Ala Gly Thr Thr Arg Ala Gly Tyr
            530                 535                 540

Pro Tyr Asn Tyr Asn Thr Thr Ala Ser Asp Gln Ile Leu Ile Glu Asn
545                 550                 555                 560

Ala Ala Gly His Arg Val Ala Ile Ser Thr Tyr Thr Thr Ser Leu Gly
                565                 570                 575

Ala Gly Pro Ala Ser Ile Ser Ala Val Gly Val Leu Ala Pro His Ser
            580                 585                 590

Ala Leu Ala Val Leu Glu Asp Thr Val Asp Tyr Pro Ala Arg Ala His
            595                 600                 605

Thr Phe Asp Asp Phe Cys Pro Glu Cys Arg Thr Leu Gly Leu Gln Gly
            610                 615                 620

Cys Ala Phe Gln Ser Thr Ile Ala Glu Leu Gln Arg Leu Lys Thr Glu
625                 630                 635                 640

Val Gly Lys Thr Arg Glu Ser
                645

<210> SEQ ID NO 2
<211> LENGTH: 627
<212> TYPE: PRT
<213> ORGANISM: Hepatitis E virus

<400> SEQUENCE: 2

Ser Gly Gly Ala Gly Gly Gly Phe Trp Gly Asp Arg Val Asp Ser Gln
1               5                   10                  15

```
Pro Phe Ala Leu Pro Tyr Ile His Pro Thr Asn Pro Phe Ala Ala Asp
            20                  25                  30

Ile Val Ser Gln Ser Gly Ala Gly Thr Arg Pro Arg Gln Pro Pro Arg
        35                  40                  45

Pro Leu Gly Ser Ala Trp Arg Asp Gln Ser Gln Arg Pro Ser Ala Ala
    50                  55                  60

Pro Arg Arg Arg Ser Ala Pro Ala Gly Ala Ala Pro Leu Thr Ala Val
65                  70                  75                  80

Ser Pro Ala Pro Asp Thr Ala Pro Val Pro Asp Val Asp Ser Arg Gly
                85                  90                  95

Ala Ile Leu Arg Arg Gln Tyr Asn Leu Ser Thr Ser Pro Leu Thr Ser
                100                 105                 110

Ser Val Ala Ser Gly Thr Asn Leu Val Leu Tyr Ala Ala Pro Leu Asn
            115                 120                 125

Pro Leu Leu Pro Leu Gln Asp Gly Thr Asn Thr His Ile Met Ala Thr
    130                 135                 140

Glu Ala Ser Asn Tyr Ala Gln Tyr Arg Val Val Arg Ala Thr Ile Arg
145                 150                 155                 160

Tyr Arg Pro Leu Val Pro Asn Ala Val Gly Gly Tyr Ala Ile Ser Ile
                165                 170                 175

Ser Phe Trp Pro Gln Thr Thr Thr Thr Pro Thr Ser Val Asp Met Asn
            180                 185                 190

Ser Ile Thr Ser Thr Asp Val Arg Ile Leu Val Gln Pro Gly Ile Ala
    195                 200                 205

Ser Glu Leu Val Ile Pro Ser Glu Arg Leu His Tyr Arg Asn Gln Gly
    210                 215                 220

Trp Arg Ser Val Glu Thr Thr Gly Val Ala Glu Glu Ala Thr Ser
225                 230                 235                 240

Gly Leu Val Met Leu Cys Ile His Gly Ser Pro Val Asn Ser Tyr Thr
                245                 250                 255

Asn Thr Pro Tyr Thr Gly Ala Leu Gly Leu Leu Asp Phe Ala Leu Glu
                260                 265                 270

Leu Glu Phe Arg Asn Leu Thr Pro Gly Asn Thr Asn Thr Arg Val Ser
            275                 280                 285

Arg Tyr Thr Ser Thr Ala Arg His Arg Leu Arg Arg Gly Ala Asp Gly
290                 295                 300

Thr Ala Glu Leu Thr Thr Thr Ala Ala Thr Arg Phe Met Lys Asp Leu
305                 310                 315                 320

His Phe Thr Gly Thr Asn Gly Val Gly Glu Val Gly Arg Gly Ile Ala
                325                 330                 335

Leu Thr Leu Phe Asn Leu Ala Asp Thr Leu Leu Gly Leu Pro Thr
                340                 345                 350

Glu Leu Ile Ser Ser Ala Gly Gly Gln Leu Phe Tyr Ser Arg Pro Val
            355                 360                 365

Val Ser Ala Asn Gly Glu Pro Thr Val Lys Leu Tyr Thr Ser Val Glu
    370                 375                 380

Asn Ala Gln Gln Asp Lys Gly Ile Thr Ile Pro His Asp Ile Asp Leu
385                 390                 395                 400

Gly Asp Ser Arg Val Val Ile Gln Asp Tyr Asp Asn Gln His Glu Gln
                405                 410                 415

Asp Arg Pro Thr Pro Ser Pro Ala Pro Ser Arg Pro Phe Ser Val Leu
                420                 425                 430
```

```
Arg Ala Asn Asp Val Leu Trp Leu Ser Leu Thr Ala Ala Glu Tyr Asp
            435                 440                 445

Gln Ala Thr Tyr Gly Ser Ser Thr Asn Pro Met Tyr Val Ser Asp Thr
    450                 455                 460

Val Thr Phe Val Asn Val Ala Thr Gly Ala Gln Ala Val Ala Arg Ser
465                 470                 475                 480

Leu Asp Trp Ser Lys Val Thr Leu Asp Gly Arg Pro Leu Thr Thr Ile
                485                 490                 495

Gln Gln Tyr Ser Lys Thr Phe Tyr Val Leu Pro Leu Arg Gly Lys Leu
            500                 505                 510

Ser Phe Trp Glu Ala Gly Thr Thr Arg Ala Gly Tyr Pro Tyr Asn Tyr
        515                 520                 525

Asn Thr Thr Ala Ser Asp Gln Ile Leu Ile Glu Asn Ala Ala Gly His
    530                 535                 540

Arg Val Ala Ile Ser Thr Tyr Thr Thr Ser Leu Gly Ala Gly Pro Ala
545                 550                 555                 560

Ser Ile Ser Ala Val Gly Val Leu Ala Pro His Ser Ala Leu Ala Val
                565                 570                 575

Leu Glu Asp Thr Val Asp Tyr Pro Ala Arg Ala His Thr Phe Asp Asp
            580                 585                 590

Phe Cys Pro Glu Cys Arg Thr Leu Gly Leu Gln Gly Cys Ala Phe Gln
        595                 600                 605

Ser Thr Ile Ala Glu Leu Gln Arg Leu Lys Thr Glu Val Gly Lys Thr
    610                 615                 620

Arg Glu Ser
625

<210> SEQ ID NO 3
<211> LENGTH: 660
<212> TYPE: PRT
<213> ORGANISM: Hepatitis E virus

<400> SEQUENCE: 3

Met Cys Pro Arg Val Val Leu Leu Leu Phe Phe Val Phe Leu Pro Met
1               5                   10                  15

Leu Pro Ala Pro Pro Ala Gly Gln Pro Ser Gly Arg Arg Arg Gly Arg
            20                  25                  30

Arg Ser Gly Gly Ala Gly Gly Gly Phe Trp Gly Asp Arg Val Asp Ser
        35                  40                  45

Gln Pro Phe Ala Leu Pro Tyr Ile His Pro Thr Asn Pro Phe Ala Ala
    50                  55                  60

Asp Ile Val Ser Gln Ser Gly Ala Gly Thr Arg Pro Arg Gln Pro Pro
65                  70                  75                  80

Arg Pro Leu Gly Ser Ala Trp Arg Asp Gln Ser Gln Arg Pro Ser Ala
                85                  90                  95

Ala Pro Arg Arg Arg Ser Ala Pro Ala Gly Ala Ala Pro Leu Thr Ala
            100                 105                 110

Val Ser Pro Ala Pro Asp Thr Ala Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Ser Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
                165                 170                 175
```

```
Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
            245                 250                 255

Gly Trp Arg Ser Val Glu Thr Thr Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
            290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
            325                 330                 335

Gly Thr Ala Glu Leu Thr Thr Thr Ala Ala Thr Arg Phe Met Lys Asp
            340                 345                 350

Leu His Phe Thr Gly Thr Asn Gly Val Gly Glu Val Gly Arg Gly Ile
            355                 360                 365

Ala Leu Thr Leu Phe Asn Leu Ala Asp Thr Leu Leu Gly Gly Leu Pro
            370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
            405                 410                 415

Glu Asn Ala Gln Gln Asp Lys Gly Ile Thr Ile Pro His Asp Ile Asp
            420                 425                 430

Leu Gly Asp Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Ala Thr Tyr Gly Ser Ser Thr Asn Pro Met Tyr Val Ser Asp
            485                 490                 495

Thr Val Thr Phe Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
            515                 520                 525

Ile Gln Gln Tyr Ser Lys Thr Phe Tyr Val Leu Pro Leu Arg Gly Lys
            530                 535                 540

Leu Ser Phe Trp Glu Ala Gly Thr Thr Arg Ala Gly Tyr Pro Tyr Asn
545                 550                 555                 560

Tyr Asn Thr Thr Ala Ser Asp Gln Ile Leu Ile Glu Asn Ala Ala Gly
            565                 570                 575

His Arg Val Ala Ile Ser Thr Tyr Thr Thr Ser Leu Gly Ala Gly Pro
            580                 585                 590
```

```
Ala Ser Ile Ser Ala Val Gly Val Leu Ala Pro His Ser Ala Leu Ala
            595             600             605

Val Leu Glu Asp Thr Val Asp Tyr Pro Ala Arg Ala His Thr Phe Asp
    610             615             620

Asp Phe Cys Pro Glu Cys Arg Thr Leu Gly Leu Gln Gly Cys Ala Phe
625             630             635             640

Gln Ser Thr Ile Ala Glu Leu Gln Arg Leu Lys Thr Glu Val Gly Lys
            645             650             655

Thr Arg Glu Ser
            660
```